United States Patent [19]

Imai et al.

[11] Patent Number: 5,470,534
[45] Date of Patent: Nov. 28, 1995

[54] ANALYTICAL SYSTEM USEFUL IN DIAGNOSIS OF THE CONDITION OF A DISEASE

[75] Inventors: Kyoko Imai; Kazumichi Imai, both of Katsuta; Yasushi Nomura, Mito, all of Japan

[73] Assignee: Hitachi, Ltd., Tokyo, Japan

[21] Appl. No.: 236,134

[22] Filed: May 2, 1994

[30] Foreign Application Priority Data

May 10, 1993 [JP] Japan ................................ 5-108107

[51] Int. Cl.⁶ ................................................ G01N 35/02
[52] U.S. Cl. ........................... 422/67; 422/63; 422/64; 422/70; 422/73; 436/43; 436/47; 436/48; 436/50; 436/55
[58] Field of Search ........................... 422/63, 64, 65, 422/67, 68.1, 105, 70, 73; 436/43, 47, 50, 55, 180, 48

[56] References Cited

U.S. PATENT DOCUMENTS

| | | | |
|---|---|---|---|
| 4,281,387 | 7/1981 | Kraft et al. | 364/497 |
| 4,612,289 | 9/1986 | Furuta et al. | 436/34 |
| 4,668,617 | 5/1987 | Furuta et al. | 435/4 |
| 4,781,891 | 11/1988 | Galle et al. | 422/64 |
| 5,037,612 | 8/1991 | Takahashi et al. | 422/64 |
| 5,051,238 | 9/1991 | Umetsu et al. | 422/64 |
| 5,100,622 | 3/1992 | Mimura et al. | 422/67 |
| 5,118,605 | 6/1992 | Urdea | 435/6 |
| 5,175,086 | 12/1992 | Takekawa et al. | 435/7.92 |
| 5,183,638 | 2/1993 | Wakatake | 422/64 |
| 5,215,714 | 6/1993 | Okada et al. | 422/64 |

FOREIGN PATENT DOCUMENTS 2-92300  4/1990  Japan .

*Primary Examiner*—James C. Housel
*Assistant Examiner*—Long V. Le
*Attorney, Agent, or Firm*—Fay, Sharpe, Beall, Fagan, Minnich & McKee

[57] ABSTRACT

In a first measurement stage, reaction solutions of samples are optically measured by a biochemical analyzer, and the measurement result of the analysis item which is an index of the disease status regarding the samples is compared with the check index. This check index is stored in memory beforehand. When the measurement result corresponds to the check index, the sample processing goes to a second measurement stage for measuring a specific item. In the second measurement stage, the sample is measured by an immuno-assay apparatus or a nucleic acid analyzer, and the measurement result is outputted.

9 Claims, 4 Drawing Sheets

FIG. 2

| NO. | 1ST | CHECK INDEX | 2ND | DEVICE |
|---|---|---|---|---|
| 1 | GOT | 200-300 | γ-GTP | A |
|   | GPT | >35 | ALP | A |
|   | GOT | >GPT | LAP | A |
| 2 | GOT | 20-200 | HBSAG | B |
|   | GPT | 100-500 |   |   |
| 3 | GOT | 200-3000 | HBSAG | B |
|   | GPT | 200-3000 |   |   |
| 4 | TG | >148 | LDL-GENE | C |
|   | CHO | >230 |   |   |
| 5 | CHO | >230 | LDL-CHO | A |
|   |   |   | HDL-CHO | B |
| 6 | GLU | >110 | HBAIC | D |
|   |   |   | T4 | B |

16 JAN 93
SECOND STAGE MENU          SAMP NO. ____

ANALYTICAL SYSTEM USEFUL IN DIAGNOSIS OF THE CONDITION OF A DISEASE

BACKGROUND OF THE INVENTION

The present invention relates to an analytical system which is useful in the diagnosis of a disease, and more particularly to an analytical system which is most suitable for measuring a plurality of analysis items of biological samples.

A conventional procedure for obtaining analysis data of a biological sample by a doctor so as to learn the condition of a disease of a patient is as described. First, blood is gathered from the patient so as to conduct a screening test. To measure the biological samples with an automated analyzer, for example, a biochemical analyzer as disclosed in U.S. Pat. No. 5,037,612 or an immuno-assay apparatus as described in U.S. Pat. No. 5,051,238 can be used.

Next, the doctor makes a preliminary diagnosis in consideration of the analysis data which is obtained as a result of the screening test. When the preliminary diagnosis shows that there is a possibility of a disease, blood is gathered from the patient again. The biological samples are used for specific tests so as to have an accurate grasp of the condition of a disease. The doctor makes a final diagnosis on the basis of the results of the specific tests.

To execute the specific tests, in addition to the aforementioned prior art, for example, a gene assay as shown in U.S. Pat. No. 5,118,605 (corresponding to Japanese Patent Application Laid-Open No. 2-92300) can be applied.

According to the aforementioned procedure, after the first blood gathering date, it is necessary for the patient to go the hospital for a second blood gathering. In addition, it is necessary that the doctor make a preliminary diagnosis on the basis of the primary test results and a definite diagnosis on the basis of the secondary test results on different days. This conventional method may be greatly painful for the patient and inefficient for the doctor.

SUMMARY OF THE INVENTION

An object of the present invention is to provide an analytical system in which, on the basis of the measurement results of a sample in the first measurement stage, measurements are executed with the same sample automatically in the second measurement stage.

Another object of the present invention is to provide an analytical system in which measurements can be executed in the first measurement stage and second measurement stage with a biological sample which is gathered from a patient once.

Still another object of the present invention is to provide an analytical system in which measurements can be executed with samples by biochemical assay, immuno-assay, or nucleic acid assay as required, and analysis data useful in the diagnosis of a disease can be obtained.

According to the present invention, objects of analysis or inspection are biological samples, such as blood and serum, which are gathered from a patient. For these samples, processing such as addition of reagents, transferring of reaction solutions, detection of substances formed by reaction, etc. is automatically performed.

Samples derived from patients may be classified into samples having a possibility of a disease and samples having no possibility of a disease, depending on the measurement results in the first measurement stage for measuring index analysis items or extraction items. The measurement results obtained in the first measurement stage are compared with the predetermined check level or check index. When the possibility of a disease is high as a result, corresponding samples are used as objects to be analyzed in the second measurement stage.

In the second measurement stage, a specific analysis item or assay item from which the name of a disease can be more surely determined is measured. In this second measurement stage, the immuno-assay, nucleic acid assay, or chromatography, which is different from the biochemical analysis applied in the first measurement stage, is applied for sample measurement as required.

The check level or check index which is a basis for deciding the measurement results in the first measurement stage is inputted so as to be stored in the memory of the system via an input device by an operator of the analytical system before starting the operation of the sample processing. Whenever the sample test data becomes necessary, the check index can be inputted. However, the values which are inputted once previously can be used as subsequent check indexes.

When the check index is to be inputted, the system is instructed by an operator so that a condition setting menu for the second measurement stage is displayed on a display screen such as a CRT. The check index is representative of the activity or concentration of the extraction item, or the amplitude of an electrical signal thereof, for instructing a possibility of a disease, and is inputted from the input device so that the measurement result of the index item or extraction item in the first measurement stage can be instructed as a value within a specific value range or beyond a specific limit. The check index varies with the kind of index item, and thus the analysis item to be measured in the second measurement stage can be selected or determined in accordance with the values of the check index.

The measurement results of specific analysis items in the second measurement stage are outputted to an output device such as a printer. It is desirable that the measurement results in the second measurement stage as well as the measurement results in the first measurement stage be outputted so that corresponding results are displayed in relation to each other. The doctor can then diagnose the name of a disease in consideration of the measurement result of a specific analysis item.

BRIEF DESCRIPTION OF THE DRAWINGS

FIG. 2 is a drawing showing an example of a condition setting menu for the second measurement stage displayed on the display device of the embodiment of FIG. 1.

DESCRIPTION OF THE PREFERRED EMBODIMENTS

Figure 1:
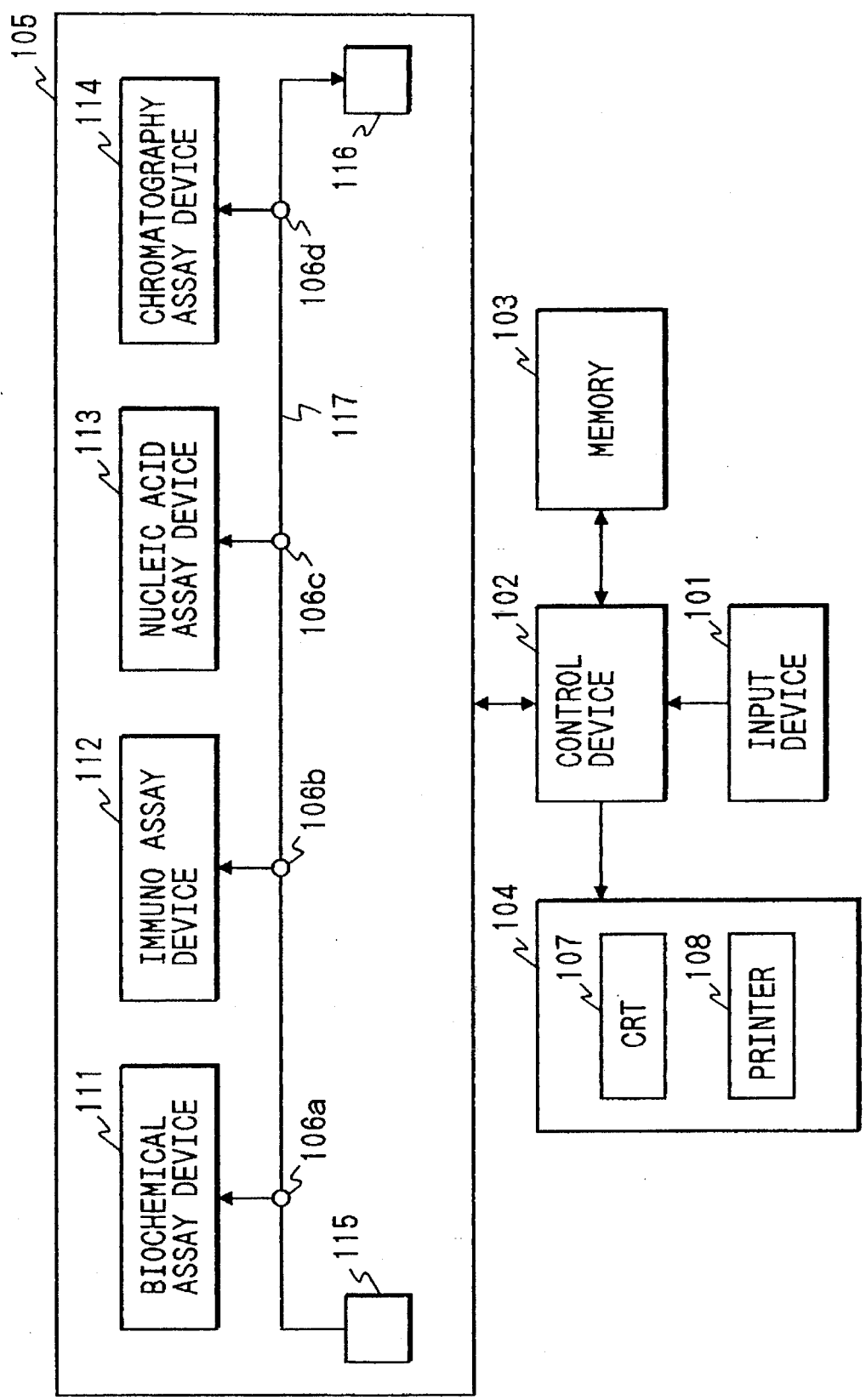
FIG. 1 is a block diagram showing a schematic constitution of an analytical system according to an embodiment of the present invention.

An embodiment of the present invention will be explained with reference to FIGS. 1 to 3. The analytical system shown in FIG. 1 has a composite analytical section 105 which can execute measurements in the first measurement stage and second measurement stage continuously. The composite analytical section 105 consists of a biochemical assay device 111 for reacting components in blood and serum samples to reagents chemically and measuring the reaction solution photochemically; an immuno-assay device 112 for measuring an antigen or antibody in the samples photochemically using an immuno-reaction; a nucleic acid assay device 113 for detecting the existence of a particular oligonucleotide sequence in the samples using labeled nucleotides as a reagent; and a chromatography assay device 114 for separating and detecting glycated hemoglobin in the samples by chromatography. Actual sample processing in the devices 111, 112, and 113 is the same as that shown in FIG. 4 or FIG. 5 which will be described later.

The composite analytical section 105 consists of a sample supply station 115, a sample storage station 116, and a common sampler including sampling pipetters 106a to 106d. A sample cup containing a sample to be analyzed is transferred on a transfer path 117 to the station 116 from the station 115.

A control device 102 controls the operation of each device in the system, processes measured data obtained in each assay device, and can output the processing results to a display device 104. An input device 101 can input various data necessary for sample analysis processing to the control device 102, and the inputted information is stored in a memory 103. Various menus stored in the memory 103 are displayed on a CRT 107 by an instruction of an operator from the input device 101. By operating the keyboard of the input device 101 while the menu screen is displayed on the CRT 107 of the display device 104, the measuring conditions are registered and changed. The measurement results are outputted to a printer 108 of the display device 104. When index items are measured in the first measurement stage, a sample cup from the supply station 115 in the common sampler is transferred so as to stop at the position of the pipetter 106a, and a part of the sample to be analyzed by the biochemical assay device 111 is introduced in this position.

When the measurement result of the index item taken up by the assay device 111 corresponds to the check index for the item, the sample cup which produces such a result is transferred so as to stop at one of the pipetters 106a, 106b, 106c, and 106d according to the analysis item which is selected for the second measurement stage. Into one of the assay devices specified according to the analysis item for the second measurement stage, a part of the sample in the sample cup is introduced by the corresponding pipetter.

When the measurement result of the index item for the first stage by the assay device 111 does not correspond to the check index for the first stage, the sample cup which produces the result is transferred to the storage station 116 without being stopped and collected at the position of any pipetter.

Before allowing the composite analytical section 105 to execute an analytical operation, an operator sets sample cups in the supply station 115 and operates the input device 101 so as to call the condition setting menu screen for the second measurement stage on the CRT 107 from the memory 103 at the same time.

"NO." on the screen shown in FIG. 2 indicates the type which is classified according to the condition of a disease. "1ST" on the screen indicates an index analysis item which can be analyzed in the first measurement stage. "CHECK INDEX" on the screen indicates the condition for judging that an analysis in the second measurement stage is necessary due to the measurement result in the first measurement stage or the extent of error, and is specified by a numeric range or a limit value. This check index is a standard for specifying an analysis item in the second measurement stage and is inputted from the input device 101 by an operator. Furthermore, a value of this check index which is registered once can be changed by the operator thereafter. Inputted data of the check index is stored in the memory 103 in correspondence with the analysis item of "1ST."

"2ND" on the screen shown in FIG. 2 indicates specific analysis items for the second stage which are selected according to differences in the check index. These specific analysis items are decided for each type. "DEVICE" on the screen indicates the assay device for analyzing the analysis item selected in the column of "2ND." Device A indicates the biochemical assay device 111, Device B indicates the immuno-assay device 112, Device C indicates the nucleic acid assay device 113, and Device D indicates the chromatography assay device 114. The analytical function displayed in the column of "DEVICE" depends on the type of assay device to be used in this analytical system, so that it can be changed freely by an operator.

When all the conditions are set on the menu and there is no need to change them, an operator calls the sample number to be analyzed in the column on the upper right side of the screen and selects the type number to be tested which is requested by a doctor. By repeating the operation for calling a sample number sequentially on the screen and selecting a type number, each sample is associated with the analysis item in the first stage and the analysis item in the second stage, and the conditions for all the samples are registered in the memory 103.

The following types of hepatitis are known: chronic hepatitis caused by alcoholic hepatic inferior, chronic hepatitis caused by virus, and acute hepatitis caused by virus. To detect a possible type of one of these diseases, GOT and GPT are selected as objects to be measured as analysis items in the first measurement stage. In the case of chronic hepatitis caused by alcohol which corresponds to Type 1 shown in FIG. 2, the active value of GOT is high, such as 200 to 300 IU (international unit). For such a sample, the active value of GPT is higher than the normal value, though the extent of increase is not high. As a result, the value of GOT is larger than the value of GPT. For such a sample, gamma-GTP, ALP, and LAP are selected as objects to be measured in the second measurement stage. In the case of chronic hepatitis caused by alcohol, the value of gamma-GTP is high, such as 50 to 400 IU, and the values of ALP and LAP are higher than the upper limits of the normal values.

In the case of chronic hepatitis caused by virus which corresponds to Type 2 shown in FIG. 2, the active value of GOT is high, such as 20 to 200 IU and the active value of GPT is also high, such as 100 to 500 IU. For such a sample, antigen of HBsAg is selected as an object to be measured in the second measurement stage. In the case of chronic B virus hepatitis, HBsAg is positive.

In the case of acute hepatitis caused by virus which corresponds to Type 3 shown in FIG. 2, the active values of both GOT and GPT are extremely high, such as 200 to 3000 IU. For such a sample, antigen of HBsAg is selected as an object to be measured in the second measurement stage. In the case of acute hepatitis, HBsAg is positive.

When definite data for specifying a disease cannot be obtained in the second measurement stage (for example, when the measurement result is a false positive), the analytical system can execute a third measurement stage. For example, when the measurement result of HBsAg for Type 3 is a false positive, the corresponding sample is measured by the nucleic acid assay device 113 and whether virus DNA exists or not is ascertained.

When familial hyperlipemia corresponding to Type 4 shown in FIG. 2 is doubtful, the biochemical assay device 111 is used for the first measurement stage and the nucleic acid assay device 113 is used for the second measurement stage. In this case, a sample in which the value of TG in the first measurement stage is higher than the upper limit of the normal range from 35 to 148 mg/dl, and in which the value of CHO is higher than the upper limit of the normal range from 130 to 230 mg/dl, is sent to the second measurement stage. In the second measurement stage, an LDL receptor gene is examined to ascertain whether this gene is abnormal or not.

When nephrosis corresponding to Type 5 shown in FIG. 2 is doubtful, the biochemical assay device 111 is used for the first measurement stage and the assay device 111 and the immuno-assay device 112 are used for the second measurement stage. A sample in which the concentration of CHO is higher than 230 mg/dl in the first measurement stage is sent to the second stage. In this second stage, LDL-CHO and HDL-CHO are measured. In the case of nephrosis, the value of LDL-CHO is increased and the value of HDL-CHO is normal or decreased.

When diabetes mellitus or hyperthyroidism corresponding to Type 6 shown in FIG. 2 is doubtful, the biochemical assay device 111 is used so as to measure GLU in the first measurement stage and the immuno-assay device 112 and the chromatography assay device 114 are used so as to measure thyroxine (T4) and glycated hemoglobin respectively in the second measurement stage. In the case of diabetes mellitus, the measured value of the A1c component of glycated hemoglobin becomes high. In the case of hyperthyroidism, the measured value of T4 becomes high.

Next, an analytical operation when hepatitis is doubtful in a patient will be explained.

An operator of the analytical system calls a condition setting menu screen as shown in FIG. 2 on the CRT 107, and inputs the sample number to be measured and then check indexes for type 1, type 2, and type 3, respectively. Next, the operator inputs the assay devices for measuring the analysis items gamma-GTP, ALP, LAP, and HBsAg in the second measurement stage. The operator operates the input device 101 so as to register the conditions of types 1 to 3 for the sample concerned in the memory 103. This procedure can be executed repeatedly for another plurality of samples.

Figure 3:
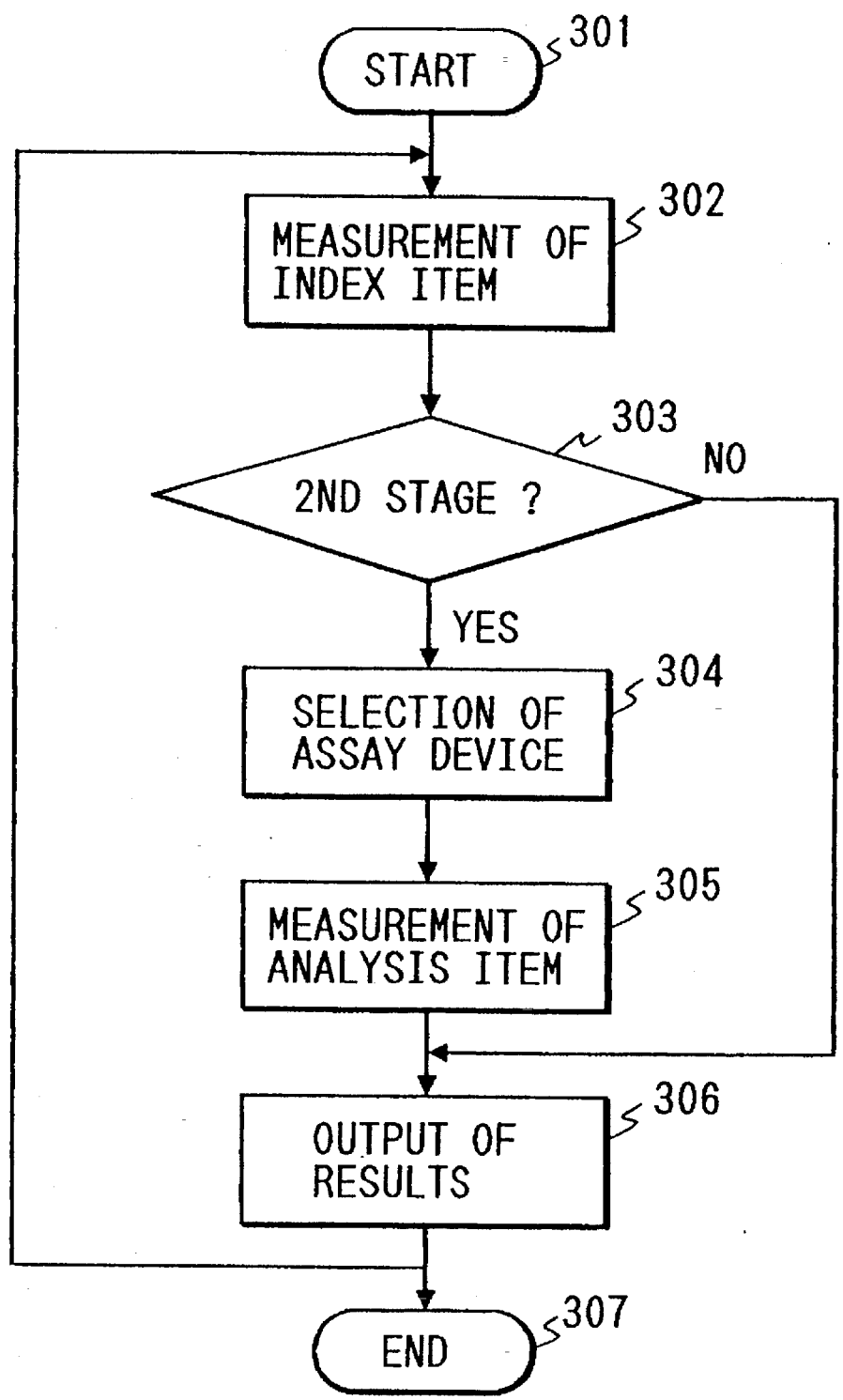
FIG. 3 is a flow chart showing the essential section of the processing of the control device of the embodiment shown in FIG. 1.

When the aforementioned preparation is completed, the operator issues a START instruction to the composite analytical section 105 at Step 301 shown in FIG. 3 so as to start the analytical operation. At Step 302, a sample is supplied to the biochemical assay device 111 by the pipetter 106a and GOT and GPT are measured.

Step 303 is a step for determining an analysis item for the second measurement stage and Step 304 is a step for selecting an assay device. When the measured values of GOT and GPT correspond to the check index of type 1, it is determined by the control device 102 to analyze gamma-GTP, ALP, and LAP by the assay device 111 in the first measurement stage, and the corresponding sample is supplied to the assay device 111. When the measured values of GOT and GPT correspond to the check indexes of type 2 or type 3, it is determined by the control device 102 to analyze HBsAg by the immuno-assay device 112 in the second measurement stage, and the corresponding sample is supplied to the assay device 112. When the measured values of GOT and GPT do not correspond to any of the check indexes of types 1 to 3, the sample cup is collected in the sample storage station 116.

At Step 305, the analysis item selected for the second measurement stage is measured by the assay device specified according to each type. At Step 306, the control device 102 activates the printer 108 so as to output the measured results obtained in the first measurement stage and the measured results obtained in the second measurement stage in correspondence with each analysis item. When any other samples to be analyzed remain, the same operation is repeated. When no sample to be analyzed remains, the analytical system goes to Step 307 and ends the operation.

Figure 4:
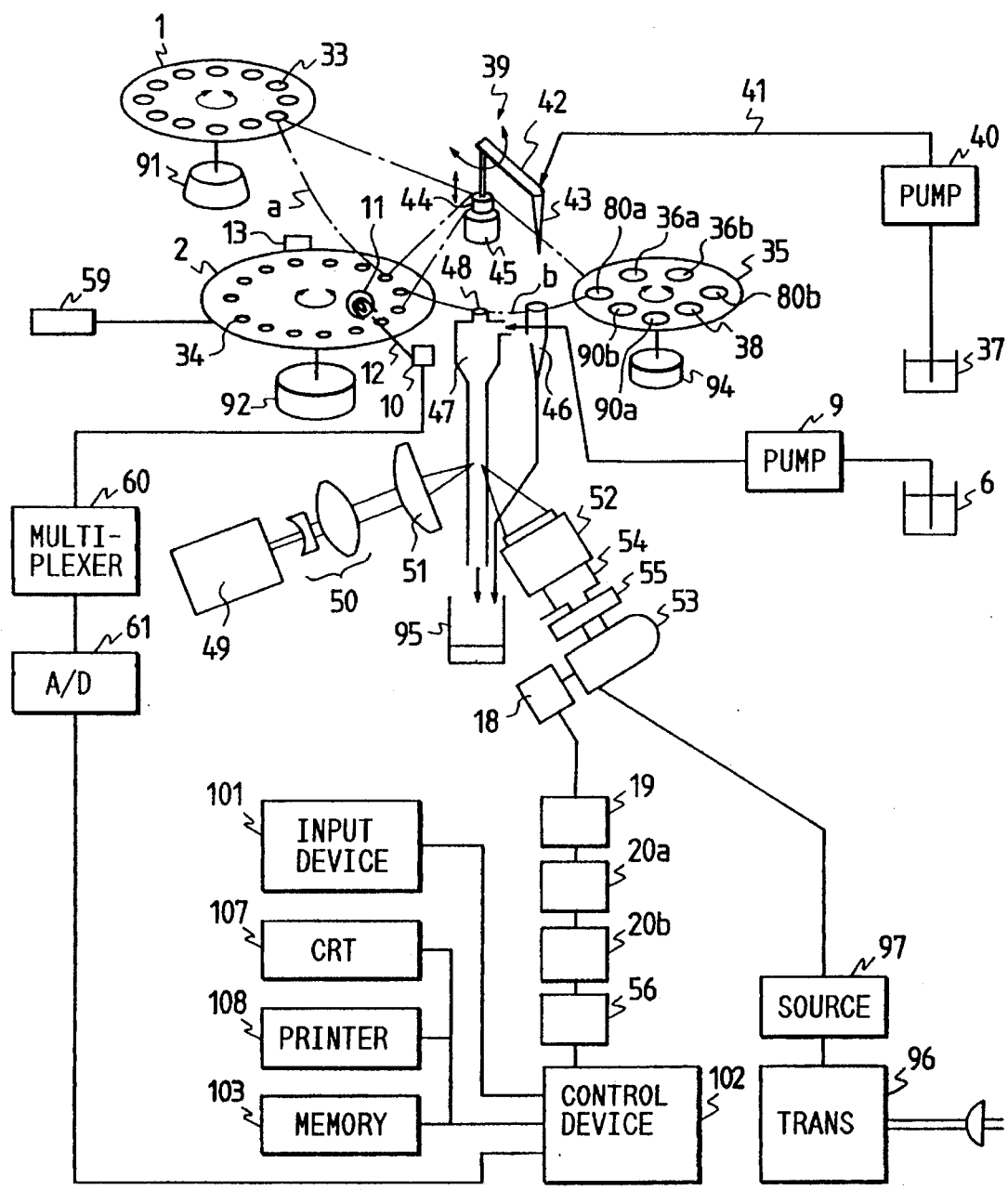
FIG. 4 is a block diagram showing a schematic constitution of an analytical system according to another embodiment of the present invention.

FIG. 4 shows a schematic constitution of another embodiment of the present invention. In the analytical system shown in FIG. 4, the biochemical assay function and nucleic acid assay function are shared by many sections. The input device 101, the control device 102, the memory 103, the CRT display 107, and the printer 108 shown in FIG. 4 have the same functions as those in the embodiment shown in FIG. 1. A sample table 1, a reaction table 2, a reagent table 35, and a pipetting mechanism 39 are operated in the first and second measurement stages.

In FIG. 4, the sample turntable 1 is a table for holding a plurality of sample cups 33 containing samples such as serum. The reaction turntable 2 is a rotatable table for holding a plurality of reaction cups 34 in a circle, which serve as measurement cells.

The plurality of reaction cups 34 are kept at a fixed temperature by a reaction isothermal water bath (not shown in the drawing) which is installed under the reaction table 2. The sample table 1 and the reaction table 2 are driven and turned by pulse motors 91 and 92, which are controlled by the controller 102 so as to stop a predetermined sample cup 33 and a predetermined reaction cup 34 at predetermined positions, respectively.

A magnet 13 is installed outside the reaction table 2 and in a predetermined area neighboring the rotation circle of the reaction cups 34. The lines of magnetic force of the magnet 13 act on a reaction cup 34 passing through the predetermined area.

A light source lamp 11 is installed at a predetermined position inside the periphery of the reaction table 2, and a spectroscope 10 is installed at a predetermined position outside the periphery so that the light source lamp 11 and the spectroscope 10 are opposite to each other across a reaction cup 34. The spectroscope 10 is of a multi-wavelength concurrent photometry type having a plurality of detectors, and functions as a photometer in the first measurement stage.

The system is structured so that when the reaction table 2 is turning, the train of reaction cups 34 crosses light flux 12 from the light source lamp 11 to the spectroscope 10. When the reaction turntable 2 is stopped, the light flux 12 penetrates through the center of the reaction cup 34 at a predetermined position measured clockwise from the sample discharge position.

The reagent turntable 35 is a rotatable table for holding various reagent solution cups necessary for analysis. It is turned by a pulse motor 94 which is controlled by the controller 102 and stops a predetermined reagent cup at the suction position in the necessary timing.

The reagent table 35 holds various reagent solution cups in a circle neighboring the periphery thereof. The various reagent solution cups include cups 80a and 80b containing reagents necessary for measuring biochemical analysis as a first analytical component, cups 90a and 90b containing magnetic particle marking probe solutions corresponding to various analysis items necessary for analyzing nucleic acids as a second analytical component, cups 36a and 36b containing fluorescent particle marking probe solutions, a cup 38 containing a restricted enzyme solution, and cups containing necessary buffer solutions (not shown in the drawing).

It is most suitable to use magnetic fine particles and fluorescent fine particles as labeled particles. As fluorescent fine particles, latex particles or inorganic particles which are covered with a fluorescent material layer on each surface are used, and a mixture of a particle forming composition substance and fluorescent substance which is grained may be used. In this case, the most suitable diameter of fluorescent fine particles is 0.1 to 1.0 μm.

The automatic pipetting mechanism consists of a pipetting mechanism body 39, a syringe pump 40 connected to the pipetting mechanism body 39 via a conduit 41, and a cleaning solution bath 37 connected to the syringe pump 40 for collecting a cleaning solution which serves as an extrusion solution. The pipetting mechanism body 39 consists of a pipetting nozzle 43 for sucking or discharging a reagent or sample, and a movable arm 42 to which the nozzle 43 is mounted. The movable arm 42 is driven by a horizontal rotation drive unit 45 and a vertical movement drive unit 44 which are controlled by the controller 102.

As the movable arm 42 operates, the nozzle 43 can rotate so as to move to a predetermined sample cup position on the sample table 1, a predetermined reaction cup position on the reaction table 2, a predetermined reagent cup position on the reagent table 35, a flow cell 47 through which a solution to be measured is passed, or a nozzle cleaning bath 46. The rotation tracks thereof are circular arcs "a" and "b." At each of the aforementioned positions, the nozzle 43 can move down or up.

The sheath flow cell 47 is a flow sight meter for measuring fine particles in a solution to be measured which flows through the inner empty section thereof. At the top of the flow cell 47, an injection chamber entrance 48 is installed and the nozzle 43 enters the injection chamber entrance 48 and discharges the solution to be measured into the flow cell 47.

A sheath solution flowing along the inner wall of the flow cell 47 is fed at a fixed flow rate from a sheath solution bath 6 by a solution feed pump 9, and ejected from the flow cell 47 into a waste solution collector 95 installed under the flow cell 47. After reaction, the solution to be measured flows in the middle of the flow of the sheath solution.

The measuring section is as shown below.

A laser beam source 49 emits an argon laser beam flux with an oscillation wave length of 488 nm and the laser beam flux is spread in beam width by a beam expander 50, focused by a lens 51, and irradiated to the flow cell 47 so as to be focused to the flow of the solution to be measured. The laser beam flux is irradiated to the flow cell 47, and, to focus fluorescence emitted by it, for example, an object lens 52 for a microscope is used.

In front of a photoelectric-detecting photomultiplier 53, a space filter 54 and a wave length selection filter 55 are installed so as to remove scattered light and Raman light.

The output of the photomultiplier 53 is amplified by a preamplifier 18 and then by a linear amplifier 19, and noise is removed by a lower limit amplitude discriminator 20a and an upper limit amplitude discriminator 20b. Thereafter, a pulse between two threshold values is integrated by a counter 56.

A high voltage is applied to the photomultiplier 53 via a transformer 96 and a high voltage power source 97. Sample numbers, counting results, analytical curves, and histograms of fluorescence measurement are outputted to the CRT display 107, the printer 108, and the memory 103. The counter 56, the display 107, the printer 108, and the memory 103 are connected to and controlled by the controller 102.

Next, the operation of the analysis system relating to the embodiment shown in FIG. 4 will be explained.

First, the sample table 1 turns, and each sample cup 33 is transferred to the sample suction position, where a fixed amount of sample is sucked from the sample cup 33 at the suction position by the nozzle 43.

The reaction table 2 turns and the fixed amount of sample in the nozzle 43 is discharged into the reaction cup 34 that has been transferred to the sample discharge position.

Next, the reaction table 2 turns and transfers the specific reaction cup 34 in which the sample is disposed to the first reagent dispensing position so as to measure the biochemical component in the first stage.

A fixed amount of first reagent for measuring the first component in the reagent cup 80a on the reagent table 35 is sucked by the nozzle 43 and dispensed into the reaction cup 34 at the reagent dispensing position on the reaction table 2. As a result, a chemical reaction develops between the sample and first reagent in the reaction cup 34.

When the dispensing operation is finished, the reaction table 2 turns through an arc of 360° plus the pitch of a reaction cup, that is, in a cycle counterclockwise, and stops.

When the reaction table 2 is turning, each reaction cup 34 on the reaction table 2 passes through the light flux 12.

When each reaction cup 34 passes through the light flux 12, the light absorption is measured by the spectroscope 10.

The measurement is repeated by the spectroscope 10 for a fixed period of time, for example, a cycle of 20 seconds, until the mixed solution is drained by a draining device 59.

When a second reagent for measuring the first stage is necessary, assuming the time when the reaction table 2 is turning and stopped as, for example, 20 seconds, the above operation is repeated in a cycle of 20 seconds.

Namely, a specific reaction cup 34 moves forward from the position when the reaction table 2 is stopped by a pitch of a reaction cup counterclockwise as the cycle goes on and stops at the second reagent dispensing position.

Into the specific reaction cup 34 at the second reagent dispensing position, the second reagent is dispensed from the reagent cup 80b on the reagent table 35 by the nozzle 43.

By doing this, the sample, first reagent, and second reagent are dispensed into the specific reaction cup 34 and a chemical reaction develops.

When the dispensing operation in the first stage is finished, the reaction table 2 again turns through an arc of 360° plus a pitch of a reaction cup, that is, in a cycle counterclockwise, and stops.

When the reaction table 2 is turning, the light flux 12 passes through the above reaction cup 34 on the reaction table 2.

When the light flux 12 passes through each reaction cup 34, the light absorption is measured by the spectroscope 10.

For a signal value of the spectroscope 10, a signal with a necessary measurement wave length is selected by a multiplexer 60 and the concentration of the analytical component in the first stage is obtained.

A concentration signal is read into the controller 102 by an A-D converter 61 and compared with the check index, and whether component analysis in the second stage is necessary or not is decided. The result is stored in the read and write memory 103.

Next, analysis of a nucleic acid in the second stage will be explained using an example of HBV, that is, hepatitis B virus.

An analysis item is specified by the type of particle probe which is added after the starting operation.

In the particle marking probe solution cup 90a, a magnetic latex particle reagent in which single stranded HBV-DNA probe type 1 is fixed is prepared.

In the fluorescent particle marking probe solution cup 36a, on the other hand, a fluorescence magnetic latex particle reagent in which single stranded HBV-DNA probe type 2 is bonded to fluorescent latex particles containing coumarin derivative as a fluorescent substance is prepared.

Each of the single stranded HBV-DNA probes, that is, single stranded HBV-DNA probe type 1 and single stranded HBV-DNA probe type 2, has a complementary nucleotide sequence for the nucleic acid component to be measured, though they have no complementary nucleotide sequence with respect to each other.

As a restriction enzyme, for example, HaeIII, which is a restriction enzyme for cutting off double stranded DNA formed by hybridizing single stranded HBV-DNA probe type 2 bonded to fluorescence marking latex particles and the nucleic acid component to be measured, is prepared.

When the analysis operation is started, the sample dispensed from the sample cup 33 by the nozzle 43 is injected into the reaction cup 34.

Next, the magnetic latex particle reagent is dispensed from the magnetic latex particle reagent solution cup 90a by the nozzle 43 and discharged into the specific reaction cup 34 in which the sample is injected.

By doing this, HBV-DNA in the sample is bonded to and reacted on the magnetic latex particles in which single stranded HBV-DNA probe type 1 is fixed. The specific reaction cup 34 is kept in the reaction state on the reaction table at a predetermined temperature, for example, at 37° C., for a fixed period of time, for example, for 15 minutes.

Next, a fixed amount of fluorescence marking latex particle reagent is sucked from the cup 36a on the reagent table 35 by the nozzle 43 and discharged into the corresponding reaction cup 34. The reaction cup 34 is kept in the reaction state on the reaction table 2 at a predetermined temperature, for example, at 37° C., for a fixed period of time, for example, for 15 minutes.

By doing this, single stranded HBV-DNA probe type 2 is reacted on the substances formed by reaction with the magnetic latex particles.

When the specific reaction cup 34 is transferred into a predetermined area in the neighborhood of the reaction cup 34 where the magnet 13 is installed, the magnetic latex particles, hybridized substances formed by reaction, and unreacted magnetic latex particles are adsorbed to the inner wall of the reaction cup 34 by the action of the magnet 13, and unreacted fluorescence marking latex particles are isolated in the solution.

The unreacted fluorescence marking latex particles are cleaned by a cleaning solution discharged from the nozzle 43 and the cleaning solution is ejected from the reaction cup 34.

In the same manner, the cleaning solution is discharged into a reaction cup 34 and then ejection of the cleaning solution is repeated.

As a result, excess fluorescence marking latex particles are ejected from the reaction cup 34.

Next, by turning the reagent table 35, the restriction enzyme cup 38 is moved to the suction position on the reagent table 35.

A fixed amount of solution containing restriction enzyme HaeIII25 in the restriction enzyme cup 38 is sucked by the nozzle 43 and discharged into the corresponding reaction cup 34 on the reaction table 2.

In the reaction cup 34, the double stranded DNA which is formed by hybridizing single stranded HBV-DNA probe type 2 bonded to fluorescence marking latex particles and the nucleic acid component to be measured is cut off at a predetermined cutting position.

By doing this, fluorescence marking latex particles are isolated in the solution in the reaction cup 34. Such an isolation reaction requires a predetermined time, for example, 15 minutes.

The solution to be measured containing the isolated substances is sucked by the nozzle 43 and discharged into the sheath flow cell 47. Isolated particles in the flow cell 47 are counted and the concentration of nucleic acid of the second component is obtained.

What is claimed is:

1. An analytical system for analyzing a biological sample which is gathered from a patient once, the system comprising:

means for storing an index analysis item of the biological sample to be measured in a first measurement stage, an assay item of the biological sample to be optionally measured in a second measurement stage following said first measurement stage, and a check level;

means for measuring the index analysis item of the biological sample in the first measurement stage;

determining means for determining whether to measure the assay item of the biological sample in the second measurement stage, which is different from the index analysis item of the first measurement stage, on the basis of a comparison of data of the measured index analysis item with the check level;

means for measuring the assay item of the biological sample in the second measurement stage responsive to said determining means determining that the assay item should be measured; and means for outputting data of the measured assay item.

2. An analytical system according to claim 1, wherein said output means includes display means for displaying the index analysis item of the biological sample to be measured in the first measurement stage, the assay item of the biological sample to be measured in the second measurement stage, and an appropriate value providing a criterion for said determining means to employ in determining whether to measure the assay item of the biological sample on the basis of results of the comparison employed by said determining means.

3. An analytical system according to claim 2, further comprising input means for inputting the appropriate value.

4. An analytical system according to claim 3, wherein said input means selects an assay device for carrying out a measurement operation of the assay item in the second measurement stage.

5. An analytical system according to claim 1, wherein said means for measuring the index analysis item is a biochemical assay device, and said means for measuring said assay item is an immuno-assay device or a nucleic acid assay device, said system further comprising a sample supplier which is shared by said means for measuring said index analysis item and said means for measuring said assay item.

6. An analytical system according to claim 1, wherein said means for measuring said assay item is a chromatographic assay device.

7. An analytical system according to claim 1, wherein said output means outputs the measured result of the assay item as well as the measured result of the index analysis item.

8. An analytical system for analyzing a biological sample which is gathered from a patient once, the system comprising:

biochemical analysis means and immuno-assay means for measuring analysis items of the biological sample, wherein the biochemical analysis means measures GOT and GPT as first analysis items of the biological sample in a first measurement stage;

means for storing a plurality of check indexes for finding a possibility of a disease regarding GOT and GPT;

means for determining which of the plurality of check indexes corresponds to measured results of at least one of the GOT and GPT of the biological sample, and for determining for measurement in a second measurement stage at least one of the analysis items that corresponds to the determined check index, said at least one of the analysis items being different from said first analysis items; and control means for controlling an operation of the biochemical analysis means or the immuno-assay means so as to measure at least one of the analysis items which is determined to correspond to the determined check index in said second measurement stage.

9. An analytical system according to claim 8, wherein said control means controls an operation of the immuno-assay means when both the measurement results of GOT and GPT of a sample correspond to individual ones of the check indexes.

* * * * *